United States Patent
Wilde et al.

(10) Patent No.: US 8,841,591 B2
(45) Date of Patent: Sep. 23, 2014

(54) GRATING-ENHANCED OPTICAL IMAGING

(75) Inventors: Jeffrey P. Wilde, Los Altos, CA (US); Yonina C. Eldar, Haifa (IL); Joseph W. Goodman, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 331 days.

(21) Appl. No.: 13/439,328

(22) Filed: Apr. 4, 2012

(65) Prior Publication Data

US 2012/0250032 A1 Oct. 4, 2012

Related U.S. Application Data

(60) Provisional application No. 61/471,205, filed on Apr. 4, 2011, provisional application No. 61/619,193, filed on Apr. 2, 2012.

(51) Int. Cl.
| | | |
|---|---|---|
| *G01B 9/02* | (2006.01) | |
| *G02B 27/58* | (2006.01) | |
| *G02B 21/06* | (2006.01) | |
| *G01N 21/956* | (2006.01) | |
| *G02B 21/00* | (2006.01) | |

(52) U.S. Cl.
CPC ............. *G02B 21/06* (2013.01); *G01B 9/02047* (2013.01); *G01B 2210/56* (2013.01); *G02B 27/58* (2013.01); *G01N 2021/95676* (2013.01); *G02B 21/002* (2013.01); *G01N 21/956* (2013.01)
USPC ........................................ 250/201.9; 356/521

(58) Field of Classification Search
USPC ........................................ 250/201.9; 356/521
See application file for complete search history.

(56) References Cited

U.S. PATENT DOCUMENTS

| RE38,307 E | 11/2003 | Gustafsson et al. | |
|---|---|---|---|
| 7,489,427 B2 * | 2/2009 | Ezura et al. | 359/10 |
| 7,619,794 B2 * | 11/2009 | Baba | 359/32 |
| 2007/0018154 A1 | 1/2007 | Bae et al. | |
| 2008/0283826 A1 | 11/2008 | Zheng et al. | |
| 2010/0187515 A1 | 7/2010 | Limmert et al. | |
| 2011/0248267 A1 | 10/2011 | Wei et al. | |

FOREIGN PATENT DOCUMENTS

WO WO 2009/000237 12/2008

OTHER PUBLICATIONS

H. Dammann and K. Gortler, "High Efficiency In-Line Multiple Imaging by Means of Multiple Phase Holograms," *Optics Communications* 3, pp. 312-315 (1971).

D. Tanner and J. J. Chen. "On the Mechanism of the Reduction of Alpha-halo Ketones by 1,3-dimethyl-2-phenylbenzimidazoline-reduction by a Set-hydrogen Atom Abstraction Chain Mechanism." J. Org. Chem. 54, 3842-3846 (1989). p. 3842 only.

(Continued)

*Primary Examiner* — Tony Ko
(74) *Attorney, Agent, or Firm* — Crawford Maunu PLLC

(57) ABSTRACT

Systems, methods and devices are implemented for optical imaging. In one embodiment of the present disclosure, an optical imaging apparatus utilizes a laser-based coherent light source, and an optical device to pass grated light along an illumination direction from the laser-based coherent light source toward an object. Additionally, an illumination modulator is provided for changing angles at which the light, moving toward the object plane, reaches the object plane, and the light reaches the object plane at different angles. Further, the apparatus can include circuitry to process image-based data in response to and based on the light reaching the object plane at different angles for a user-viewable image of an object in proximity of the object plane.

20 Claims, 13 Drawing Sheets

(56) References Cited

OTHER PUBLICATIONS

Nollau, A., Pfeiffer, M., Fritz, T. & Leo, K., "Controlled n-Type Doping of a Molecular Organic Semiconductor: Naphthalenetetracarboxylic dianhydride (NTCDA) Doped with bis(ethylenedithio)-tetrathiafulvalene (BEDT-TTF)." *J. Appl. Phys.* vol. 87, pp. 4340-4343, (2000).

Maennig, B.; Pfeiffer, M.; Nollau, A.; Zhou, X.; Leo, K. And Simon, P., "Controlled p-Type Doping of Polycrystalline and Amorphous Organic Layers: Self-consistent Description of Conductivity and Field-effect Mobility by a Microscopic Percolation Model." *Phys. Rev.B*, 64, No. 195208, (2001).

Gao, W. And Kahn, a., "Controlled p-doping of Zinc Phthalocyanine by Coevaporation with Tetrafluorotetracyanoquinodimethane: a Direct and Inverse Photoemission Study." *Appl. Phys. Lett.*, vol. 79, pp. 4040, (2001).

Werner, a. G.; Li, F.; Harada, K.; Pfeiffer, M.; Fritz, T. And Leo, K., "Pryonin B as a Donor for n-type Doping of Organic Thin Films." *Appl. Phys. Lett.*, vol. 82, pp. 4495-4497, (2003).

Ouyang, J.; Xu, Q.; Chu, C.-W.; Yang, Y.; Li, G. and Shinar, J., "On the Mechanism of Conductivity Enhancement in poly(3,4-ethylenedioxythiophene):poly(styrene sulfonate) Film Through Solvent Treatment." *polymer*, 45, pp. 8443-8450, (2004).

A. Werner et al. "n-Type Doping of Organic Thin Films Using Cationic Dyes." *Adv. Funct. Materials* 14(3), 255 (Mar. 2004). Abstract only.

J. Liu et al. "Efficient bottom cathodes for organic light-emitting devices." *App. Phys. Lett.* 85(5), 837 (2004). Abstract only.

F. Li et al. "Leuco Crystal Violet as a Dopant for n-Doping of Organic Thin Films of Fullerene C60." *Phy. Chem. B* 108(44), 17076-17082 (Oct. 2004). Abstract only.

Drechsel, J.; Mannig, B.; Kozlowski, F.; Pfeiffer, M.; Leo, K. and Hoppe, H., "Efficient Organic Solar Cells Based on a Double p-i-n. Architecture Using Doped Wide-Gap Transport Layers." *Appl. Phys. Lett.*, 86, No. 244102, (2005).

S. Tanaka et al. "Doping Effect of Tetrathianaphthacene Molecule in Organic Semiconductors on Their Interfacial Electronic Structures Studied by UV Photoemission Spectroscopy." *Japanese J. Appl. Phys.* 44(6a) 3760 (2005).

Singh, T. B. et al., "Fabrication and Characterization of Solution-Processed Methanofullerene-Based Organic Field-Effect Transistors." *J. Appl. Phys.* 97, 083714, (2005).

M.G.L. Gustafsson, "Nonlinear Structured-Illumination Microscopy: Wide-Field Fluorescence Imaging with Theoretically Unlimited Resolution", *Proc. Nat. Acad. Sci.*, 102, pp. 13081-13086 (2005).

V. Mico, Z. Zalevsky, P. Garcia-Martinez and J. Garcia, "Super-resolved Imaging in Digital Holography by Superposition of Tilted Wavefronts," *Appl. Opt.* 45, pp. 822-828 (2006).

Li, F.H., et al., "Acridine Orange Base as a Dopant for n Doping of C60 Thin Films." *J. Appl. Phys.* 100, 023716, (2006).

C. Chan et al. "N-type doping of an electron-transport material by controlled gas-phase incorporation of cobaltocene." *Chem. Phys. Lett.* 431, 67 (Sep. 2006).

C. Chan et al. "Molecular n-type Doping of 1,4,5,8-naphthalene tetracarboxylic dianhydride by Pyronin B Studied Using Direct and Inverse Photoelectron Spectroscopies," *Adv. Funct. Mater.* 16, 831-837 (2006). Abstract only.

Yun, M. et al., "Capacitance-Voltage Characterization of Polyfluorene-Based Metal-Insulator-Semiconductor Diodes." *Appl. Phys. Lett.* 89, 013506, (2006).

K. Walzer et al. "Highly efficient organic devices based on electrically doped transport layers." *Chem. Rev.* 107, 1233-1271 (2007). Abstract/Table of Contents only.

Zhang, X. H.; Domercq, B. & Kippelen, B., "High-performance and Electrically Stable C-60 Organic Field-Effect Transistors." *Appl. Phys. Lett.*, 91, 092114, (2007).

Zhang, X. H. & Kippelen, B., "High-performance C60 n-Channel Organic Field-Effect Transistors Through Optimization of Interfaces." *J. Appl. Phys.* 104, 104504, (2008).

Chan, C. K.; Zhao, W.; Barlow, S.; Marder, S. and Kahn, A., "Decamethylcobaltocene as an Effieient n-Dopant in Organic Electronic Materials and Devices." *Org. Electron.*, 9, pp. 575-581, (2008).

X.Q. Zhu et al. "Hydride, Hydrogen Atom, Proton, and Electron Transfer Driving Forces of Various Five-Membered Heterocyclic Organic Hydrides." *J. Am. Chem. Soc.* 130(8), 2501-2516 (Feb. 2008). Abstract only.

P. Wöbkenberg et al., "High mobility n-channel organic field-effect transistors based on soluble $C_{60}$ and $C_{70}$ fullerene derivative." *Synthetic Metals* 158, pp. 468-472 (2008).

S. A. Shroff, J. R. Fienup and D. R. Williams, "OTF Compensation in Structured Illumination Superresolution Images," *Proc. SPIE* 7094, 709402 (2008).

A. Neumann, Y. Kuznetsova and S. R. J. Brueck, "Structured Illumination for the Extension of Imaging Interferometric Microscopy," *Opt. Exp.* 16, pp. 6785-6793 (2008).

S. A. Shroff, J. R. Fienup and D. R. Williams, "Phase-Shift Estimation in Sinusoidally Illuminated Images for Lateral Superresolution," *JOSA A* 26, pp. 413-424 (2009).

Chan, C. K.; Zhao, W.; Kahn, A. and Hill, I. G., "Influence of Chemical Doping on the Performance of Organic Photovoltaic Cells." *Appl. Phys. Lett.*, 94, No. 203306, (2009).

S. Reineke et al. "White organic light-emitting diodes with fluorescent tube efficiency." *Nature* 459, 234 (May 2009).

Yamagishi, M.; Tominari, Y.; Uemura, T. and Takeya, J., "Air-Stable n-Channel Single-Crystal Transistors with Negligible Threshold Gate Voltage." *Appl. Phys. Lett.*, 94, No. 053305, (2009).

Y. Wang et al., "Supercapacitor Devices Based on Graphene Materials," *J. Phys. Chem.* 113, pp. 13103-13107 (2009).

K. A. Mkhoyan et al., Atomic Electronic Structure of Graphene-Oxide, *Nato Lett.* 9 (3), pp. 1058-1063 (2009).

P. Meduri et al., "Hybrid Tin Oxide Nanowires as Stable and High Capacity Anodes for Li-Ion Batteries," *Nano Lett.* 9 (2), pp. 612-616 (2009).

J. H. Oh et al. "Molecular n-type doping for air-stable electron transport in vacuum-processed n-channel organic transistors." *Applied Physics Letters* 97, 243305 (Dec. 2010).

P. Wei et al. "Use of a 1*H*-Benzoimidazole Derivative as an *n*-Type Dopant and to Enable Air-Stable Solution-Processed *n*-Channel Organic Thin-Film Transistors." *J. Am. Chem. Society* 132(26), 8852-8853 (Jun. 2010). Abstract only.

Timmreck, R.; Olthof, S.; Leo, K. and Riede, M. K., "Highly Doped Layers as Efficient Electron-Hole Recombination Contacts for Tandem Organic Solar Cells." *J. Appl. Phys.*, 108, No. 033108, (2010).

Y.C. Eldar and P. Volker, "Recovering Signals From Lowpass Data," *IEEE Trans. Signal Processing*, vol. 58, No. 5, pp. 2636-2646, May 2010.

M. Mishali and Y. C. Eldar, "From Theory to Practice: Sub-Nyquist Sampling of Sparse Wideband Analog Signals," *IEEE Journal of Selected Topics on Signal Processing*, vol. 4, No. 2, pp. 375-391, Apr. 2010.

A. Faridian, et al., "Nanoscale Imaging Using Deep Ultraviolet Digital Holographic Microscopy," *Optics Express* 18 (13), pp. 14159-14164 (2010).

Meiss, J.; Menke, T.; Leo, K.; Uhrich, C.; Gnehr, W.-M.; Sonntag, S.; Pfeiffer, M. and Riede, M., "Highly Efficient Semitransparent Tandem Organic Solar Cells with Complementary Absorber Materials." *Appl. Phys. Lett.*, 99, No. 043301, (2011).

Meerheim, R.; Olthof, S.; Hermenau, M.; Scholz, S.; Petrich, A.; Tessler, N.; Solomeshch, O.; Lüssem, B.; Riede, M. and Leo, K., "Investigation of C60F36 As Low-Volatility P-Dopant in Organic Optoelectronic." *J. Appl. Phys.*, 109, No. 103102, (2001).

M. Mishali, Y. C. Eldar, O. Dounaevsky and E. Shoshan, "Xampling: Analog to Digital at Sub-Nyquist Rates," *IET Circuits, Devices & Systems* 5, pp. 8-20 (2011).

J. P. Wilde, J.W. Goodman, Y. Eldar, and Y. Takashima, "Grating-Enhanced Coherent Imaging," *Conference Paper presented at Optics in the Life Sciences: OSA Optics and Photonics Congress, Monterey, California, Apr. 4-6, 2011, Novel Techniques in Microscopy(NTM) session,* Apr. 4, 2011.

* cited by examiner

GRATING-ENHANCED OPTICAL IMAGING

RELATED DOCUMENTS

This patent document claims benefit under 35 U.S.C. §119 to U.S. Provisional Patent Application Ser. No. 61/471,205, entitled "Grating Enhanced Optical Imaging Systems" and filed on Apr. 4, 2011, and to U.S. Provisional Patent Application Ser. No. 61/619,193, entitled "Provisional Application Directed to Grating Enhanced Optical Imaging" and filed on Apr. 2, 2012; these patent documents and the Appendices filed in the underlying provisional applications are fully incorporated herein by reference.

FIELD

Aspects of the present disclosure relate generally to optical imaging such as exemplified by methods and systems benefiting from grating-enhanced imaging.

BACKGROUND

Aspects of the present disclosure relate generally to optical imaging such as exemplified by methods and systems benefiting from grating-enhanced imaging.

Optical microscopy has experienced a significant growth in the medical and biological sciences during the last decade. The increased importance of optical microscopy has been due to new developments in fluorescent probe technology, and the availability of quantitative three-dimensional image data obtained through either computational deconvolution or scanning confocal microscopy.

Optical microscopy offers several advantages over non-optical microscopy techniques. Use of optical microscopy allows viewing of living tissue samples in their natural state. Electron microscopy, in comparison, requires microscopy samples which are dried and exposed to vacuum. Additionally, the interior of the sample can be viewed and mapped in three dimensions using optical microscopy, whereas scanning electron microscopy and other scanned probe microscopies map only the surface of the sample, and thus cannot provide information about the sample interior.

For improved resolution of imaging systems, beyond the intrinsic cutoff frequency as defined by the numerical aperture and wavelength, various approaches have been previously investigated. These include the use of two static gratings, two moving gratings, structured illumination, and various oblique illumination schemes. In many instances, these techniques are burdensome/complex to implement or are limited by the numerical aperture (NA) of the illumination optics.

SUMMARY

The present disclosure is directed to apparatuses and methods involving the use of grating-enhanced optical imaging systems.

A typical application might involve the detection of defects in semiconductor mask, or die inspection. The instant invention is also applicable more generally to improving the resolution of microscopes, providing high resolution images with low-cost low-numerical-aperture lenses. Also, the working distance of this system can be greater than that of a conventional microscope with comparable resolution.

Aspects of the present disclosure are directed toward an optical imaging apparatus. The optical imaging apparatus includes a laser-based coherent light source and an optical device. The optical device is configured and arranged to pass grated light along an illumination direction from the laser-based coherent light source toward an object plane. The optical imaging apparatus further includes an illumination modulator for changing angles at which the light, moving toward the object plane, reaches the object plane, wherefrom the light reaches the object plane at different angles. The optical imaging apparatus also contains circuitry for processing image-based data in response to, and based on, the light reaching the object plane at different angles for a user-viewable image of an object in proximity of the object plane.

Additionally, the present disclosure is also directed to an optical imaging apparatus, having the following: a spatially coherent light source for illumination of an object; a grating component configured and arranged to generate N optical wavefronts containing the object's spatial amplitude variation; an imaging system having an object-space collection numerical aperture of $NA_O$; and a light-responsive device configured and arranged to detect at least N complex-amplitude images of the composite wavefronts propagating from the object and received by the imaging system.

Consistent with aspects of the present disclosure, a method for coherent and grating-enhanced imaging includes the following steps: providing a spatially coherent light source for illumination of an object; generating from a grating component N optical wavefronts containing the object's spatial amplitude variation; and using an imaging system having an object-space collection numerical aperture of $NA_O$ and using light-responsive device to detect at least N complex-amplitude images of the composite wavefronts propagating from the object and received by the imaging system.

In accordance with an example embodiment of the present disclosure, a coherent imaging technique is provided that utilizes a diffraction grating placed near the object to alias high spatial frequency information through the imaging system pupil. The resulting optical field in the image plane is detected by means of digital holography. Multiple measurements are taken with the grating shifted by a fraction of its period between exposures. Linear signal processing is then used to separate the aliased spectral components, and Fourier techniques are applied to reconstruct high-resolution images. Experimental results validate the approach, yielding an enhancement in resolution by a factor of 2.6 when using five diffracted beams (orders up to ±2).

In another example embodiment, the resolution capability of an optical imaging system can be increased through a combination of optical preprocessing (for example, a grating moved between N exposures) and digital post-processing (algorithm for unscrambling the aliasing created by the grating). This approach can provide a resolution beyond the classical resolution limit which specifies a maximum spatial frequency that can be observed through a conventional optical system, which in turn, depends on the numerical aperture of the lens and the wavelength.

In another example embodiment, an imaging system is provided in which the Fourier spectrum of an object is truncated by the aperture stop of the imaging system. Without further processing, this truncation will result in limited resolution in the image. The instant invention provides a way to recover this lost information by combing pre-processing using, for example, a series of grating, and post processing performed on one or more digital images obtained. More specifically, a high-frequency grating is placed in close contact with the object transparency, either just before the object or just after it. The grating amplitude transmittance is chosen to be periodic which results in aliasing of the spectrum of the object in the Fourier domain.

Other aspects are directed to a coherent imaging approach based on use of a single grating placed near an object in order to alias high-frequency content through the pupil. Digital holographic detection is employed to detect the complex amplitude of the signal in the image plane. Linear signal processing, similar to that used for structured illumination, can be used to reconstruct a high-resolution image, providing both intensity and phase distributions. This grating-enhanced technique can be used for non-fluorescent objects and is not limited by the numerical aperture (NA) of the illumination optics.

Further aspects and embodiments are directed to and/or are benefited from aspects including one or more of the following: a spatially coherent light source for illumination of an object; a grating component used to generate N optical wavefronts containing the object's spatial amplitude variation (e.g., where each said wavefront propagates in one of N different directions wherein the angular spectrum associated with each wavefront has a unique bias angle); an imaging system having an object-space collection numerical aperture of $NA_O$; and detection of at least N complex-amplitude images of the composite wavefronts propagating from the object and received by the imaging system (e.g., where the complex-amplitude images are acquired sequentially in at least N steps and in digital format. For example, the complex-amplitude images can be detected by digital holography.

Yet other, more detailed aspects and embodiments concern digital processing of N complex-amplitude images to construct a resultant final image with improved resolution. Resultant resolution in certain embodiments is related to a larger "effective" numerical aperture $NA_{eff}$. For example, in the case of 1-D enhancement, $NA_{eff}$ can be as large as $N*NA_O$, while for 2-D enhancement the resolution gain in a given direction depends on how the N object wavefronts are distributed in angle space. In one such more detailed embodiment, some degree of overlap of the N angular spectra is implemented to better stitch the spectra together in the presence of optical components with non-ideal properties and/or environmental perturbations to the optical system.

The above summary is not intended to describe each embodiment or every implementation of the present disclosure. The figures, detailed description and claims that follow more particularly exemplify various embodiments.

BRIEF DESCRIPTION OF THE DRAWINGS

Aspects of the present disclosure may be more completely understood in consideration of the detailed description of various embodiments of the present disclosure that follows in connection with the accompanying drawings, in which.

Figure 1:
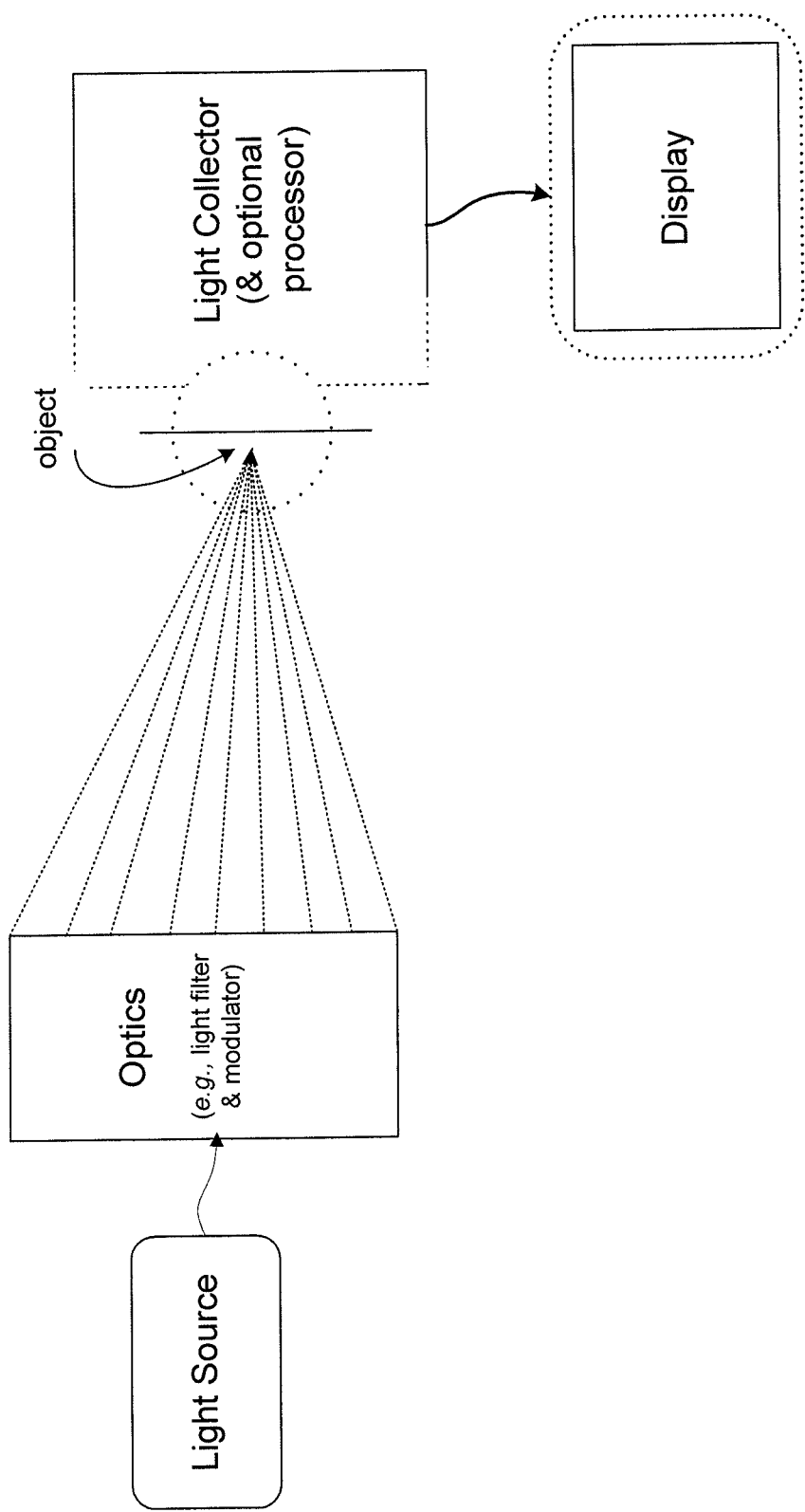
FIG. 1 shows a block diagram of a grating-enhanced optical imaging system, consistent with an example embodiment of the present disclosure.

While the present disclosure is amenable to various modifications and alternative forms, specifics thereof have been shown by way of example in the drawings and will be described in further detail. It should be understood, however, that the intention is not to limit the disclosure to the particular embodiments described. On the contrary, the intention is to cover all modifications, equivalents, and alternatives falling within the spirit and scope of the present disclosure.

DETAILED DESCRIPTION

The present disclosure is believed to be applicable to a variety of different types of devices and processes, and the present disclosure has been found to be particularly suited for optical imaging applications. While the present disclosure is not necessarily limited to such applications, various aspects of the present disclosure may be appreciated through a discussion of various examples using this context.

Consistent with certain example embodiments of the present invention, an optical imaging apparatus includes the following: a spatially coherent light source for illumination of an object; a grating component configured and arranged to generate N optical wavefronts containing the object's spatial amplitude variation; an imaging system having an object-space collection numerical aperture of $NA_O$; and a light-responsive device configured and arranged to detect at least N complex-amplitude images of the composite wavefronts propagating from the object and received by the imaging system. FIG. 1 illustrates such an apparatus or system, consistent with such embodiments of the instant disclosure.

Figure 2:
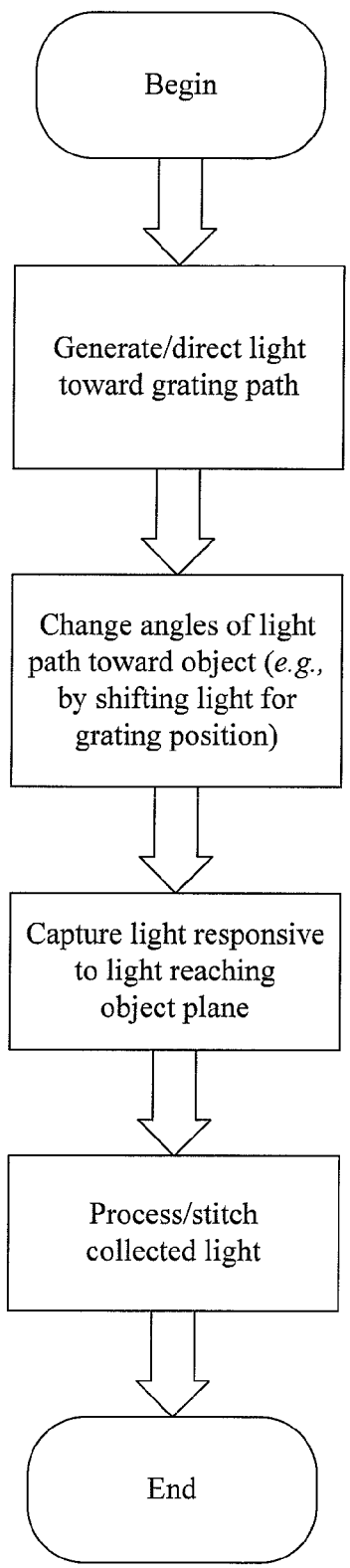
FIG. 2 shows a flow chart that exemplifies one manner of operating the optical imaging system of FIG. 1, consistent with another example embodiment of the present disclosure.

Consistent with certain aspects of the present disclosure, and as mentioned above, a method for coherent and grating-enhanced imaging includes the following steps: providing of a spatially coherent light source for illumination of an object; generating from a grating component N optical wavefronts containing the object's spatial amplitude variation; and using an imaging system having an object-space collection numerical aperture of $NA_O$ and using light-responsive device to detect at least N complex-amplitude images of the composite wavefronts propagating from the object and received by the imaging system. FIG. 2 illustrates a method consistent therewith.

In another example embodiment, an imaging system can be provided in which the Fourier spectrum of an object is truncated by the aperture stop of the imaging system. Without further processing, this truncation will result in limited resolution in the image. The instant invention provides a way to recover this lost information by combing pre-processing using, for example, a series of grating, and post processing performed on one or more digital images obtained. More specifically, a high-frequency grating can be placed in close contact with the object transparency, either just before the object or just after it. The grating amplitude transmittance is chosen to be periodic which results in aliasing of the spectrum of the object in the Fourier domain.

In the absence of grating, the finite pupil of the system can restrict the light that passes to a finite region of the spectrum, and as a consequence, information about the object detail could be lost. The effect of the grating is to multiplex many different parts of the object spectrum into the pupil. The resulting image will not resemble the object, but with a series of images (N images to expand the spectrum by a factor of N), each taken, for example, with a change in the grating position (specifically, a shift along the direction of the grating vector), it is possible to unscramble the overlapping regions of the spectrum and stitch them back together in proper order, yielding a broader spectrum of the object than could otherwise pass the pupil.

In coherent optical imaging, the angle of illumination can control the spatial frequency content that passes through the pupil of the system. For normal incidence illumination, the imaging system can act as a low-pass filter centered at zero frequency. For oblique angles, the imaging filter bandwidth remains the same, but the center frequency of the filtering operation moves away from the origin in proportion to the sine of the illumination angle.

If an object is illuminated by multiple off-axis beams, then it is possible to construct a synthetic aperture that is larger than the physical aperture, thereby yielding an enhanced image resolution. Taking such an approach, instead of using a high-NA microscope objective, allows for the use of a low-NA, low-cost objective lens. Moreover, a long working distance (several millimeters) between the object and the lens can be maintained, in contrast with a conventional high-NA objective that typically requires a very short working distance (a few hundred microns). Lastly, coherent imaging combined with coherent detection (e.g., via digital holography) can allow for both the image amplitude and phase distribution to be simultaneously recorded. One such technique uses a single grating to produce a resolution enhancement in one direction. The grating can be located very near the object and is translated in one direction in controlled steps, with the step increment being a fraction of the grating period. A typical grating period is on the order of 1 to 10 microns, therefore, precision motion is desired. The grating diffraction orders serve to produce the shifted versions of the object spectrum, but in this case the multiplicity of shifted object spectra can be generated simultaneously and therefore produces aliasing in the passband. Multiple image exposures, with the grating stepped between exposures, can be used along with linear signal post-processing to de-alias the spectra. Two-dimensional resolution enhancement is obtained by rotating the grating and repeating the multiple stepping and exposure acquisition process.

In the instant disclosure, an alternative technique for producing oblique coherent illumination in two dimensions is set forth below. Two implementations are described, both of which utilize a faceted grating array, with the grating array displaced from the object along the optical axis by several millimeters, which is comparable to the working distance of the objective lens. In addition, no motion of the grating element is needed. The faceted grating array can be a 2-D array of individual grating elements, each element having a specific grating spacing and orientation. A small-diameter collimated beam illuminates one grating element at a time. A portion of the beam can be subsequently diffracted towards the object with a unique 2-D angle (specified by polar and azimuthal angles). By sequentially illuminating each of the grating facet elements, a corresponding 2-D set of illumination angles is formed. The resulting set of shifted image spectra are no longer aliased, but they still need to be properly "stitched" together in the frequency domain to create a high-bandwidth composite spectrum. This composite spectrum is then Fourier transformed to yield a high-resolution digital image. Prior to transforming, the composite image spectrum can be multiplied by a free-space propagation transfer function to numerically implement focus control.

2-D angular manipulation of a collimated beam can be accomplished by use of a 2-D scan mirror placed in the front focal plane of a 4f telecentric imaging system, such an approach is limited in the angles that can be produced before significant aberration arises. For example, a coherent super-resolution holographic microscope in which the angle of the scanned illumination beam is limited to ±10°. Embodiments of the instant disclosure described herein can overcome this by using a faceted grating array to generate large-angle off-axis beams, thereby making the overall optical system design simpler and much less prone to aberration degradation. Illumination angles >±70° are achievable, which in turn leads to enhanced resolution performance.

Figure 3:
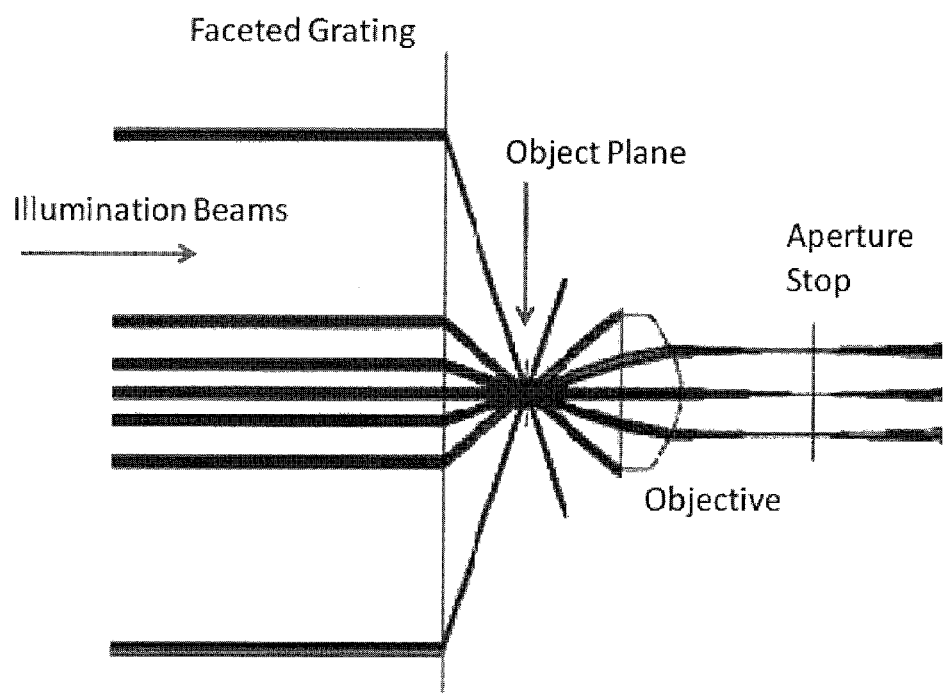
FIG. 3 depicts an objective lens and collimated beam propagation via a faceted grating array, consistent with an embodiment of the present disclosure.

FIG. 3 depicts illumination of an object by individual, small-diameter collimated beams. Beam deflection toward the object is created by using a faceted grating array or faceted diffractive optical element.

An example approach for embodiments of the instant disclosure can be seen illustrated in FIG. 3. A set of parallel collimated beams (propagating from left to right) are individually directed, one at a time, toward an object by means of a faceted grating array.

This layout is constructed using Zemax, a commercial optical design software package. The incoming collimated beams are 4 mm in diameter and have a wavelength of 633 nm. The faceted grating array can be made from elements having grating frequencies of 500, 1000 and 1500 cycles/mm. Either amplitude or phase gratings can be used, although phase gratings have the advantage of lower absorption loss. For the off-axis beams, one of the first-order diffraction beams can be utilized (the other diffracted beam propagates out of the optical system; the set of unused diffraction beams is not shown in FIG. 3). The strength of the first-order diffraction can be controlled through the shape of the grating structure. For example, a square-wave phase grating having a phase modulation of approximately $\pi$ radians will yield diffraction in which virtually all of the light is split equally between the +1 and −1 diffraction orders, with very little light remaining in the zero order or the higher orders (±2 and higher). The layout of FIG. 3 only shows beam deflection in one dimension, but it is understood that a 2-D faceted grating can be used in combination with a 2-D array of collimated beams to provide oblique illumination in two angular dimensions. In this case, the grating lines in any particular facet element of the grating array can be oriented to direct the incoming collimated beam toward the object.

The objective lens in FIG. 3 can be a molded asphere having an effective focal length of 8 mm and a useable numerical aperture of about 0.4 (e.g., manufactured by Rochester Photonics Corp. and can be purchased from Thorlabs (Part No. A240TM)). Similar lenses made by other suppliers can be used for the objective. It is desirable, although not necessary, to use a simple single-piece optical lens for the objective, one that is readily available at low cost and can be used at a working distance of several millimeters.

Figure 4:
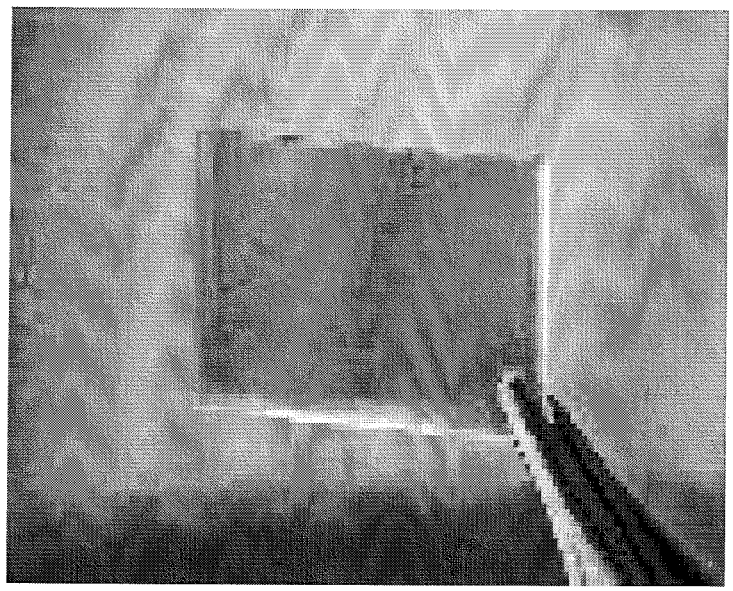
FIG. 4 shows example transmission gratings using lithography and nanopatterning techniques, consistent with an embodiment of the present disclosure.
Figure 4:
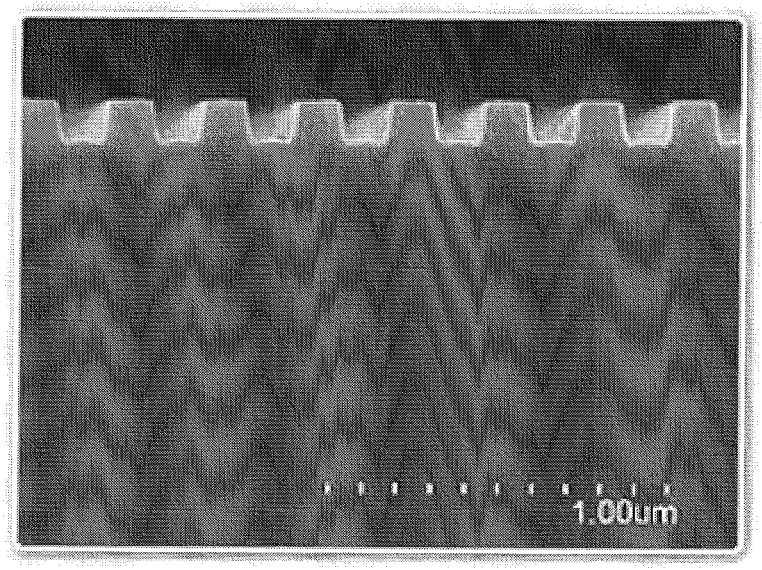

Custom faceted grating arrays can be created using standard microfabrication technology (also known as Diffractive Optical Element technology). For example, a glass or fused silica wafer can be patterned using lithography and then subsequently etched to form the desired surface profile. Alternately, a master grating can be fabricated out of silicon or glass and then used to stamp low-cost replicas in plastic or polymer-coated transparent substrates. Examples of which are shown in FIG. 4. Any of a number of companies should be able to provide a custom grating array or faceted diffractive optical element; for example, see:

1. LightSmyth (http://www.lightsmyth.com/products/index.php)
2. Holoeye (http://www.holoeye.com/diffractive_optical_elements_doe.html)
3. Jenoptik (http://www.memsoptical.com/prodserv/products/plastics.htm)
4. Rochester Photonics (http://www.rpcphotonics.com/optical.asp)
5. Holo-Or (http://www.holoor.com/index.htm)

The illumination angles shown in FIG. 3 are spaced in a nonlinear fashion, but it is the sine of the illumination angle that determines the corresponding displacement of the object spectrum within the pupil of the imaging system. The off-axis illumination angles in FIG. 1 are 18.45°, 39.27° and 71.71° with corresponding sines of 0.317, 2×0.317=0.633, and 3×0.317=0.950 which provides uniform separation of the spectrum displacements in the frequency domain.

FIG. 4 shows examples of: (top) transmission grating fabricated using lithography techniques, and (bottom) grating "nanopatterned silicon stamp," both made by LightSmyth.

The layout shown in FIG. 3 is used for illustration of the basic concept. Those skilled in the art will recognize that other operating wavelengths, beam dimensions, faceted grating array specifications, and objective lenses can be used in a similar manner.

Attention is now turned to the manner in which the collimated beam array is formed. Two approaches are described; one based on a spatial light modulator and another that uses a 2-D scanning mirror in conjunction with a lenslet array.

Figure 5:
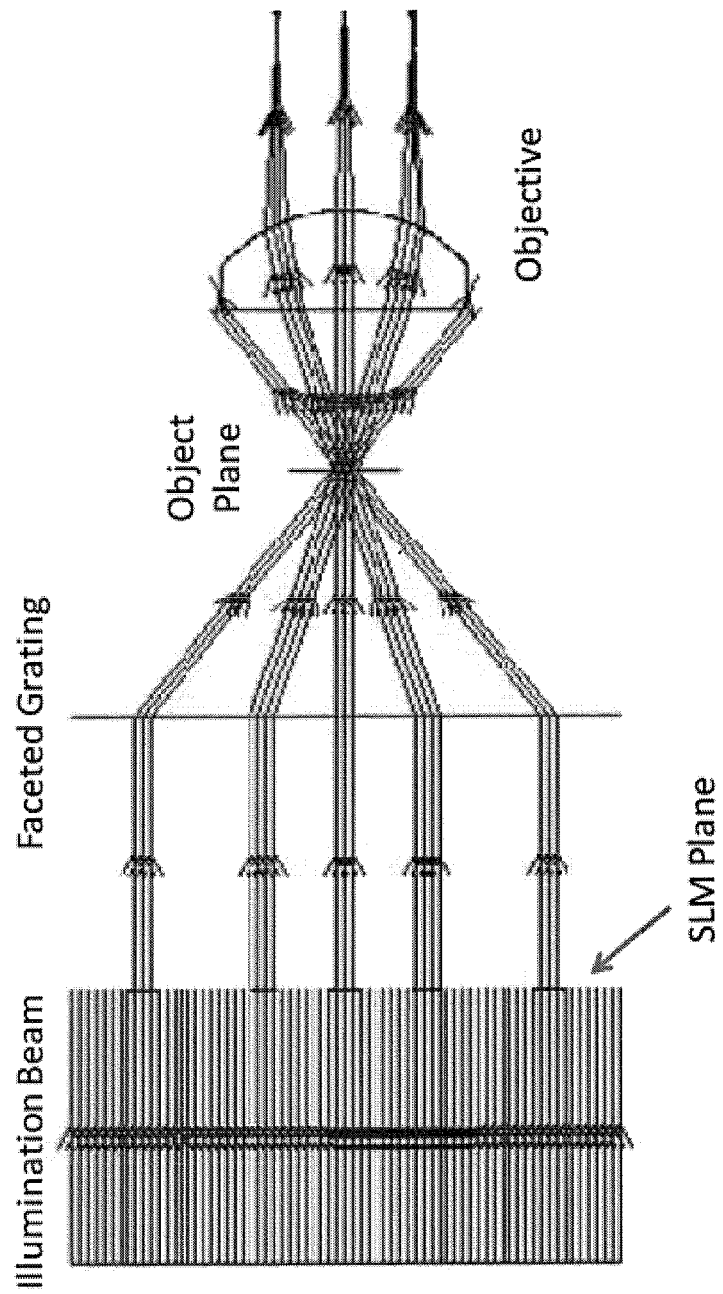
FIG. 5 shows an array of small-diameter collimated beams created and controlled by a spatial light modulator (SLM), consistent with an embodiment of the present disclosure.

One way in which a set of collimated beams can be constructed is shown in FIG. 5. In this implementation, a large-diameter collimated beam illuminates a spatial light modulator (SLM). The SLM acts like a shutter array that apertures the beam to a smaller diameter and allows this small diameter beam to pass through the system. By sequentially turning on one element of the SLM at a time, the object is sequentially illuminated by the desired set of angles.

An SLM made from liquid crystal between crossed polarizers can provide the required functionality (e.g., see products made by Boulder Nonlinear http://www.bnonlinear.com/ or by Meadowlark Optics http://www.meadowlark.com/). The pixels of the SLM may be smaller than the small-diameter beam size, but pixels can be grouped together as needed to form an electronically controlled set of apertures properly positioned within the cross section of the incoming large-diameter beam. In this way, no moving parts are needed to facilitate sequential oblique object illumination. The majority of the incoming light can be blocked at the SLM plane. As a result, this approach has high optical loss which could present an issue depending on the power of the source laser and the sensitivity of the digital camera used for image detection.

FIG. 5 shows an array of small-diameter collimated beams that is created and electronically controlled by using an amplitude SLM made, for example, using liquid crystal technology.

Figure 6:
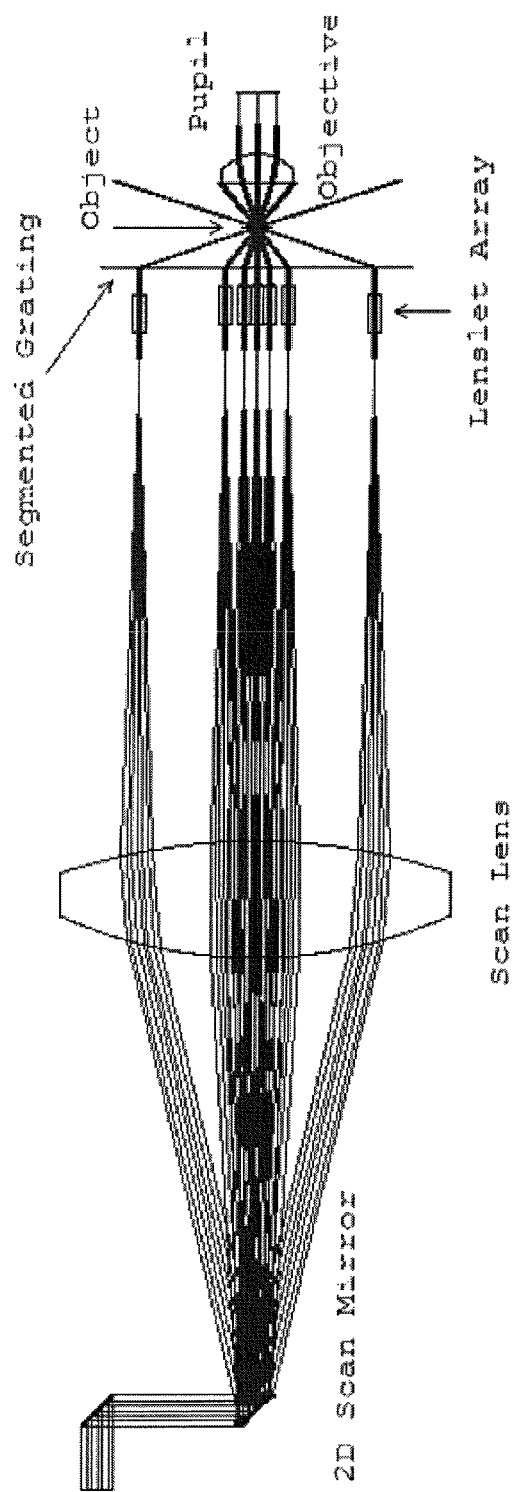
FIG. 6 depicts a 2-D scan mirror, scan lens and 2-D lenslet array and technique for illumination control, consistent with a further embodiment of the present disclosure.

An alternative embodiment that circumvents the loss problem is shown in FIG. 6. It uses a 2-D scan mirror in the front focal plane of a scan lens.

FIG. 6 illustrates a technique in which the array of small-diameter collimated beams is created by a 2-D scan mirror in conjunction with a scan lens and a 2-D lenslet array.

The 2-D scan mirror can be sequentially stepped through a set of 2-D angles, each angle corresponding to one lenslet in the lens array. In this particular design, the wavelength is 633 nm and the mirror deflection angle spans a range of ±6.8°. The scan lens brings the beam to a focus in front of the lens array, and one lenslet in the array acts to collimate the beam. The resulting small-diameter "beamlet" propagates to the faceted grating array where it diffracts from a grating element and is directed to the object. By sequentially stepping the scan mirror to each of the lenlets, a discrete set of illumination angles is formed, ranging from normal incidence to large off-axis angles of incidence (in this design the maximum angle is about 72°).

Figure 7:
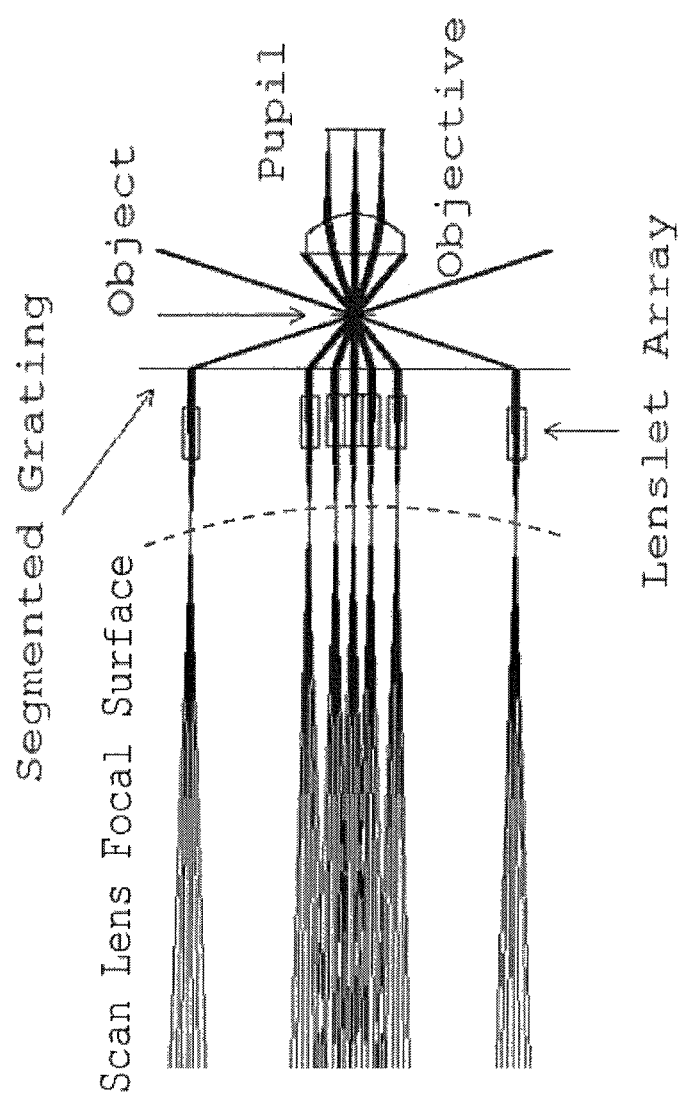
FIG. 7 shows a closer view of beam collimation and object illumination, consistent with FIG. 3 and other embodiments described herein.

FIG. 7 shows a close-up view of beam collimation and object illumination. All beams are shown together, but in practice only one beam path is active at any given time. The faceted grating is constructed with elements having frequencies of 500, 1000 and 1500 cycles/mm. Similar to the layout of FIG. 3, the maximum angle of illumination for this design is 72°, but in general the maximum angle depends on the maximum grating frequency.

Features of a scan-mirror optical design can include:

1. A telecentric scan lens design that yields a focused beam arriving at normal incidence to the lenslet array plane. The scan mirror is placed in (or close to) the front focal plane of a singlet scan lens.

2. A lenslet array that is constructed from simple plano-convex rod lenses. The flat lenslet surface faces the scan lens. The convex surface is spherical, which makes the lenslet a simple component to fabricate. The discrete lenses can be assembled into an array, for example, by using a thin mounting plate with holes drilled in the appropriate 2-D pattern. Each hole accommodates a single rod lenslet. Another plate have a 2-D matching pattern of spacers can be used to set the stand-off of each lenslet (relative to a reference plane) to ensure proper focal alignment as described in the next item. We note that the lens array could also, in principle, be fabricated as a single piece using molding, embossing or etching technology.

3. A curved scan lens focal surface, so each lenslet is placed in a specific z-position (along the direction of the optical axis). In this way, the front focal plane of each lenslet coincides with the local focus surface of the scan lens, thereby producing a collimated beamlet.

4. A faceted grating array with individual grating elements that produce two first-order diffracted beams. Either the +1 or −1 order illuminates the object; the other order is not used. Therefore, it is possible to have the optical loss of the system be in the vicinity of 3 dB (which is much lower than the SLM version described in the previous section).

Two-dimensional scan mirrors are available commercially. Examples of a small galvo mirror system and an electrostatic MEMS-based device are shown in FIG. 6. The MEMS mirror technology is less expensive, more compact, and amenable to high-volume production, but parts that support beam diameters of a few millimeters have a low resonance frequency of a few hundred hertz, so the response time is somewhat slower than the galvo technology.

Figure 8:
FIG. 8 shows commercially-available 2-D scan mirrors, consistent with aspects of the present disclosure.
Figure 8:
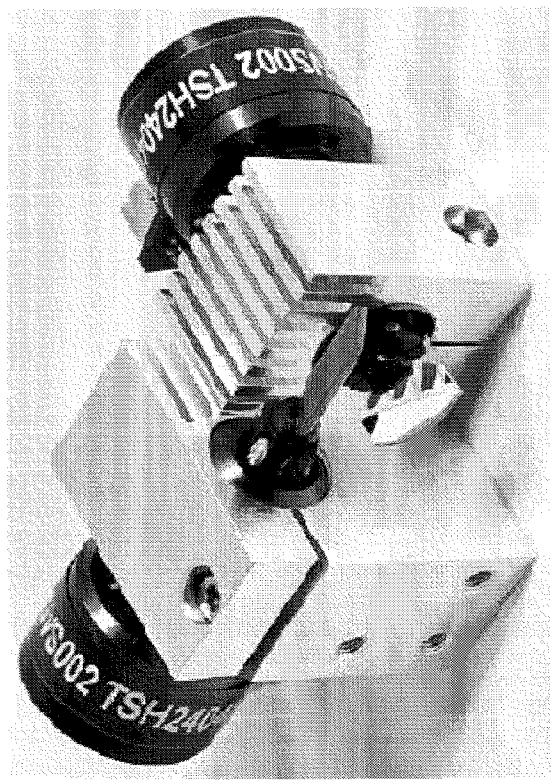

FIG. 8 shows commercially available 2-D scan mirrors: (left) dual galvo mirror system with an angular deflection of ±12.5° for beams up to 5-mm diameter, Model GVS002 sold by Thorlabs, (right) 2-D electrostatically controlled MEMS mirror with an angular deflection of ±6° for beam diameters up to 3.6-mm diameter, sold by Mirrorcle Technology, Inc.

A version of the basic architecture shown in FIG. 3, using a manually translated aperture to mimic the SLM approach of FIG. 5, is provided. The setup is illustrated below in FIG. 9.

Figure 9:
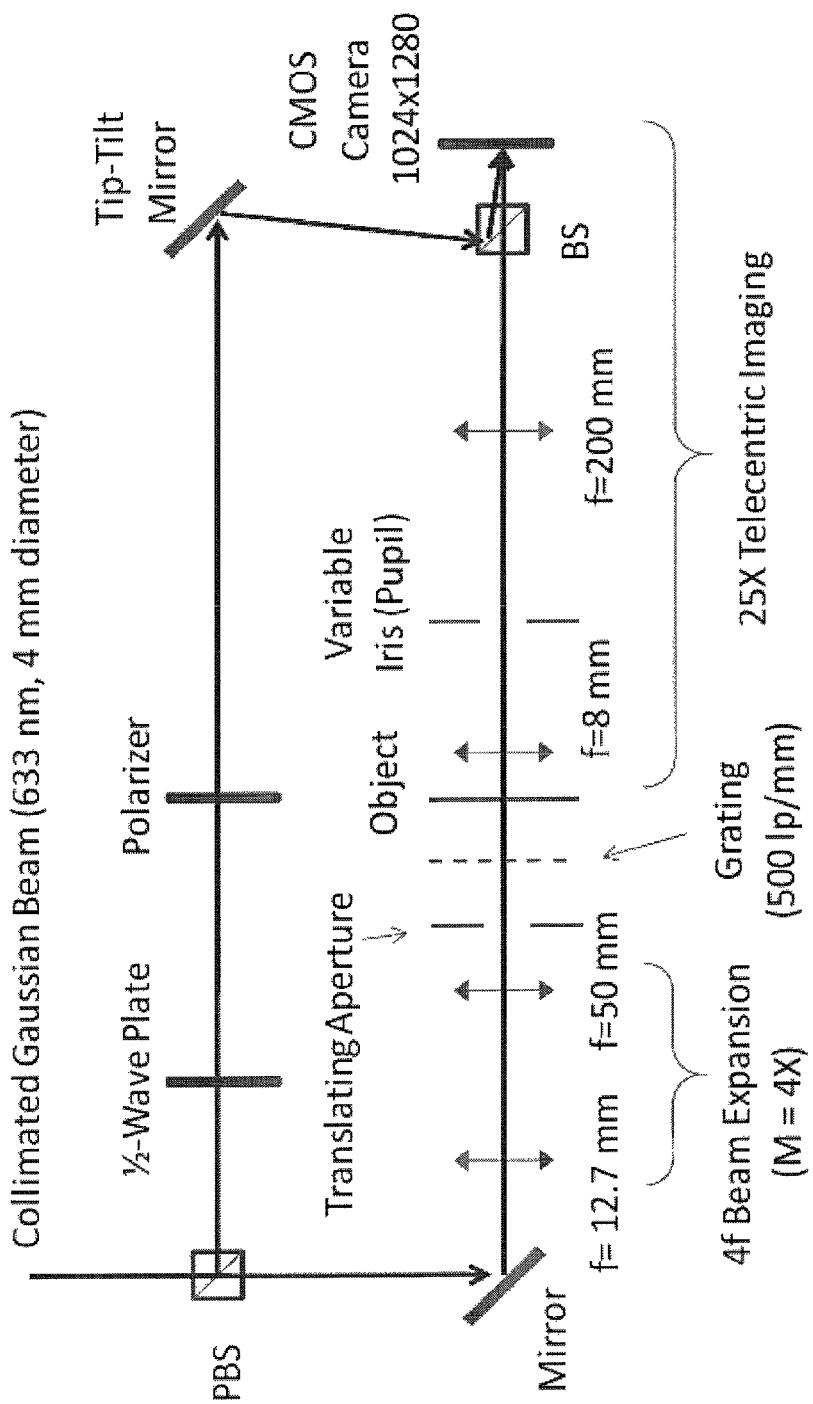
FIG. 9 depicts a grating-based optical imaging system and approach using a 2 mW He—Ne laser, in accordance with other aspects of the present disclosure.
Figure 12:
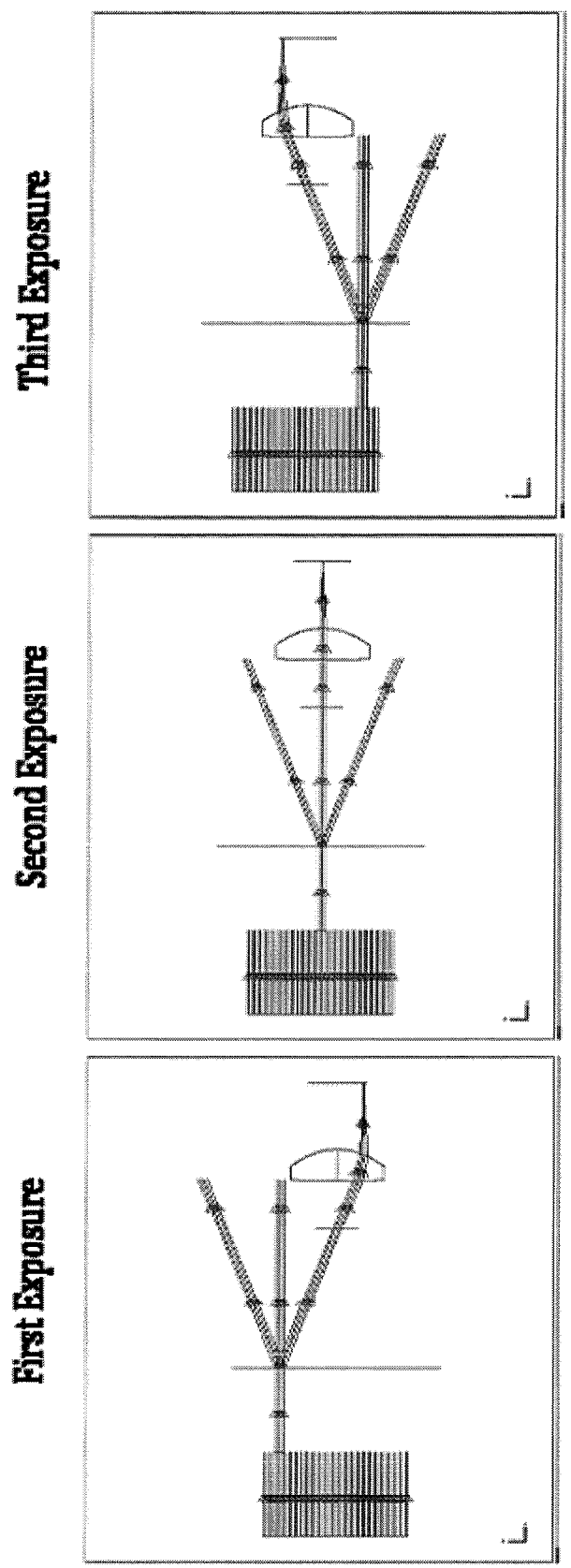
FIG. 12 depicts an apparatus and method for detecting and capturing complex-amplitude images by digital holography, in accordance with embodiments of the present disclosure.

FIG. 9 shows a demonstration layout including a source that is a 2 mW He—Ne laser. The layout includes a Mach-Zehnder interferometer with an imaging path in one arm and a reference beam in the other arm. In the imaging path, the beam can be expanded to a diameter of about 16 mm. A translating aperture of approximately 3 mm diameter can be placed on an xy stage so it can be decentered from the optical axis. A 500 lp/mm thin-film holographic grating, readily available at very low cost from Edmund Optics, follows the translating aperture. The grating can be followed by a test target placed in the object plane. The test target (e.g., Part No. MRS-4, purchased from Ted Pella, Inc., www.tedpella.com) contains various patterns and feature sizes. Some of the patterns are quasi-periodic 2-D line patterns that range from 50-um pitch down to 0.5-um pitch. The spacing between the grating and the test target is several millimeters. By translating the aperture in the transverse xy plane, as shown in FIG. 12, the 0 and ±1 orders are also translated, thereby affecting a change in object illumination angle. The microscope optics consist of a molded glass asphere objective lens (f=8 mm, NA=0.5) and a doublet tube lens (f=200 mm), yielding a magnification of 25×. The useable numerical aperture of the objective lens, within which the beam is diffraction limited, is determined to be 0.4 (by analysis of the lens design in Zemax). Therefore, an aperture stop can be placed in the back focal plane of the objective lens to limit the NA of the objective to 0.4. The optical field associated with the image is recorded as an off-axis digital hologram using a CMOS camera (1024×1280 pixels, 5.2-um pixel size, 8-bit gray level).

Figure 11:
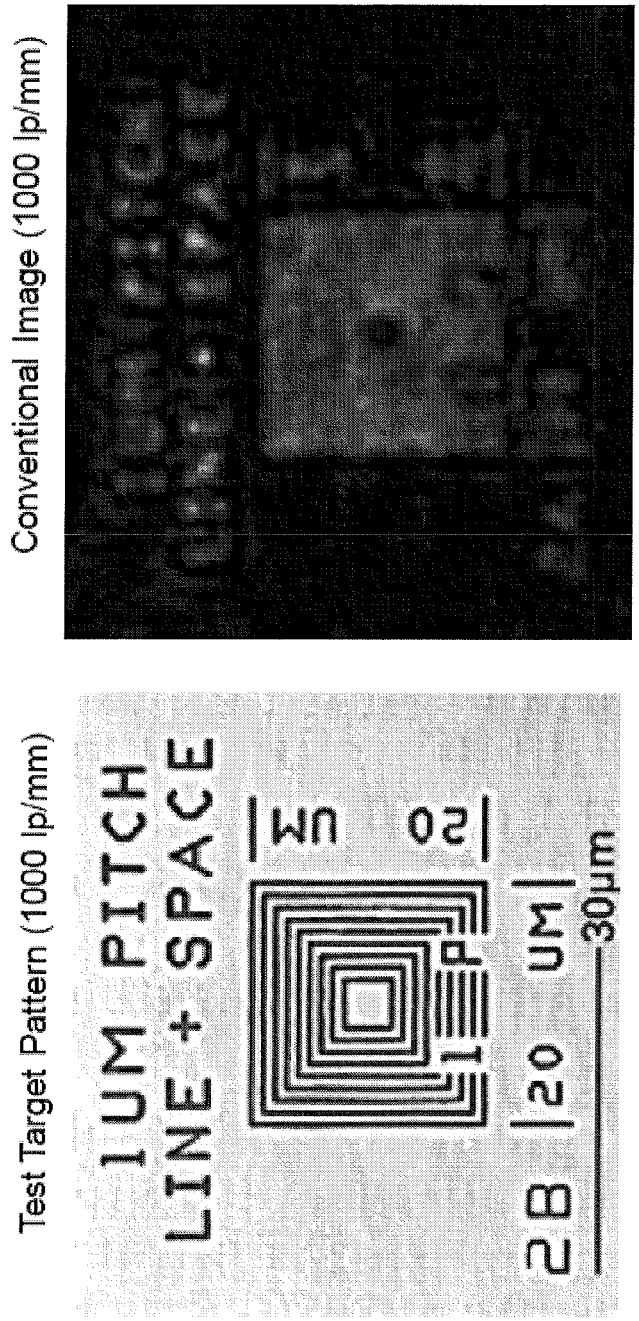
FIG. 11 shows a second test target pattern at 1000 lp/mm versus a conventional image, in accordance with aspects of the present disclosure.

Initially, just the imaging arm of the system was tested by performing conventional intensity imaging of the test target. In this case, the target was illuminated with normal incident light, and the reference beam path was blocked. The imaging system can be coherent, however, only the image intensity is detected. The coherent cutoff frequency of the imaging path is NA/λ=0.4/0.633 um=632 cycles/mm. FIG. 11 shows the result for imaging a 500 lp/mm test pattern. Because the pattern frequency is below cutoff, a reasonably good intensity image is formed as shown on the right-hand side of FIG. 11.

Figure 10:
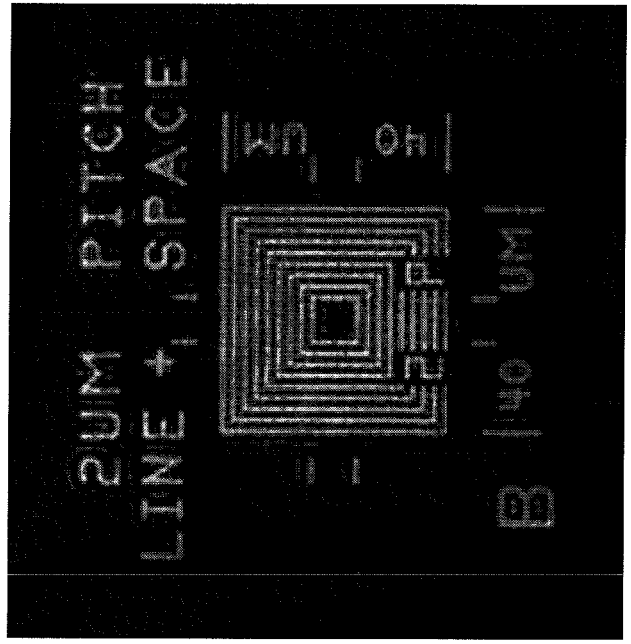
FIG. 10 shows a test target pattern at 500 lp/mm versus a conventional image, in accordance with aspects of the present disclosure.
Figure 10:
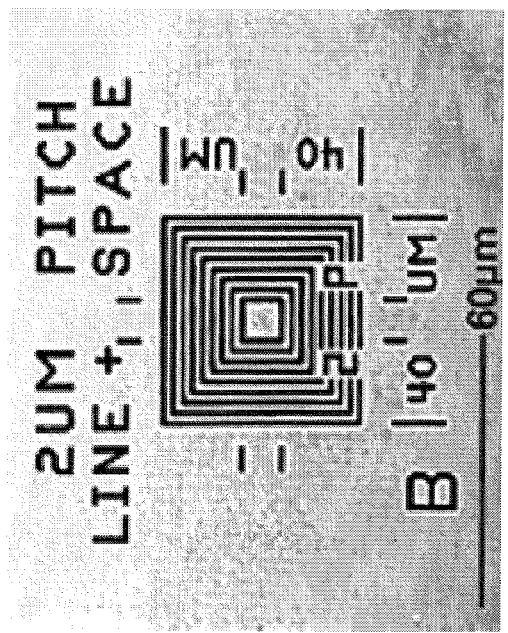

FIG. 10 shows a test target pattern (500 lp/mm, which is below the coherent cutoff frequency) used to evaluate the microscope performance. On the left is shown a picture of the nominal pattern layout taken from the supplier's website. The photo on the right is the direct detection intensity image formed using the microscope optics in FIG. 9. However, when trying to image a pattern of 1000 lp/mm, as shown in FIG. 12, the resulting image is blurred and void of detail. This result is expected given that the pattern frequency is above cutoff.

FIG. 11 shows a second test target pattern (1000 lp/mm, which is above the coherent cutoff frequency) used to evaluate the microscope performance. The conventional direct detection image, shown on the right, is clearly void of pattern detail.

In order to improve the imaging system resolution, the frequency bandwidth of the system can be enlarged by using the general approach disclosed here—namely grating-based oblique illumination and recording of the image-plane optical field for each illumination angle. As described above and below and as shown in FIG. 12, a translating aperture is used in conjunction with a 500 lp/mm grating to produce illumination at ±18.5° (±1 order beams) in addition to conventional normal incident illumination. FIG. 12 shows that the object illumination angle is changed by translating a small-diameter aperture across a larger diameter collimated beam and allowing the transmitted beam to diffract from a 500 cycles/mm thin-film grating.

The translating aperture can be moved in the horizontal (x-axis) direction. A digital hologram is captured for each of the three aperture positions. The grating can be rotated by 90° and this process is repeated in the vertical direction. The set of holograms can be numerically processed to extract the shifted image spectra. In this instance, the illumination beam for each exposure passes through the imaging pupil and shows up as a strong peak in the corresponding image spectrum. For the off-axis exposures, the location of these peaks are identified and used to displace the individual spectral sections back to their proper locations in the frequency domain. In addition, the complex amplitudes of the peaks are used to scale the spectra so that they can be properly combined and overlapped in a self-consistent manner without amplitude or phase discontinuities. The result of this process yields a higher-bandwidth composite image spectrum and a corresponding higher resolution image as shown in FIG. 13.

Figure 13:
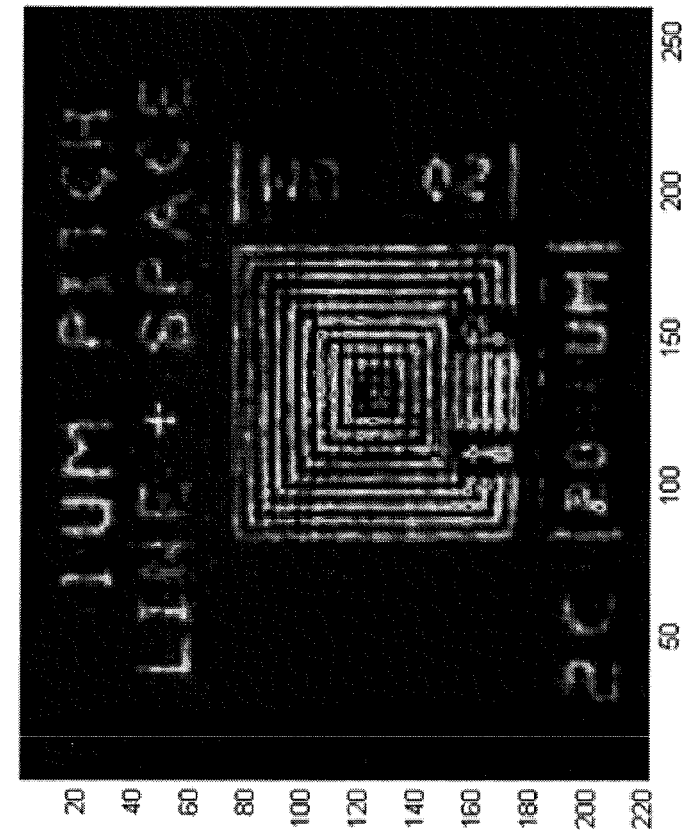
FIG. 13 depicts composite image spectrum and corresponding image intensity using grating-based oblique illumination techniques, consistent with aspects of the present disclosure.
Figure 13:
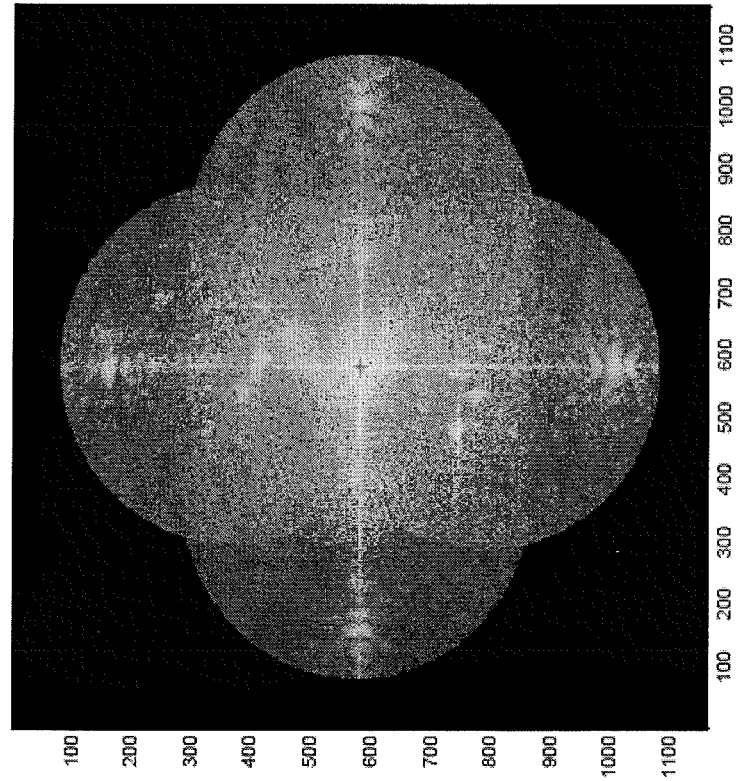

FIG. 13 shows results for the grating-based oblique illumination technique. The coherent imaging path with an intrinsic NA=0.4 is enhanced in two dimensions to yield an effective NA=0.73. The composite image spectrum is shown on the left, and the corresponding image intensity is on the right.

By comparing the enhanced image of FIG. 13 with the conventional image in FIG. 11, the synthetic aperture technique disclosed here is shown to increase the coherent cutoff frequency and yield improved resolution. Lastly, when extending this technique to higher diffraction orders that fall outside the imaging pupil, numerical processing of the spectral overlap regions (starting from the center and working outward) can be used to determine the proper location and complex amplitude scaling of the individual spectral sections.

In this section, the discussion and analysis is limited to a 1-D formulation, but an extension to 2D has been developed. For example, consider a coherent imaging system with a high-frequency grating placed in close proximity to the object being imaged, either just before the object or just after it. The grating amplitude transmittance is a periodic function with period $1/f_g$, which is represented by $P(x)$ and can be expanded in a complex Fourier series:

$$P(x) = \sum_{n=-\infty}^{\infty} p_n \exp(-j2\pi n f_g x) \tag{1}$$

Furthermore, it is assumed that the grating has been fabricated such that it possesses a finite set of lower-order Fourier coefficients $p_n$ approximately equal in magnitude, meaning that all the plane wave components illuminating the object are of approximately equal magnitude, while all the other higher-order $p_n$ are close to zero. For example, a Dammann phase grating provides such a response.

If $t_0(x)$ represents the complex amplitude transmittance of the object, which is the quantity we wish to recover, the field leaving the sandwiched object and grating is given by $$t_o(x)P(x) = t_o(x) \sum_{n=-\infty}^{\infty} p_n \exp(-j2\pi n f_g x). \quad (2)$$

The spectrum of $t_o(x)P(x)$, which is incident on the pupil plane, is then given by $$U(v) = T_o(v) \otimes \sum_{n=-\infty}^{\infty} p_n \delta(v - nf_g), \quad (3)$$

where $T_o(v)$ is the object spectrum and ⊗ signifies convolution. It is assumed that the grating is located before or in contact with the object. If the grating follows the object, then the propagating portion of the object spectrum for normal incidence should be considered.

In the absence of the grating, the finite pupil of the system can restrict the light that passes through the pupil stop to a finite region of the spectrum. Consequently, information about the object detail can be lost. The effect of the grating is to multiplex many different parts of the object spectrum into the pupil. The resulting image will not resemble the object, but with a series of images (N images to expand the spectrum by a factor ≤N), each taken with an appropriate change in the grating Fourier coefficients $p_n$, it is possible to unscramble the overlapping regions of the spectrum and stitch them back together in proper order, yielding a much broader spectrum of the object than would otherwise pass the pupil. One possible set of changes of the spectral coefficients $p_n$ can be obtained by translating the grating between image captures by a fraction of the period, in particular by $1/f_g N$. Each such translation changes the phase of the $n^{th}$ grating Fourier component by $$\Delta\emptyset_n = \frac{2\pi n}{N}.$$

This follows an approach for generating multiple modulations in the Modulated-Wiseband Converter (MWC).

In order to accomplish this extension of resolution, the complex amplitude of the field in the image plane can be measured. This can be done via digital holography by bringing in a tilted reference wave, coherent with respect to the field in the image plane, to interfere with this field and thus create a hologram. The complex field in the image plane can then be recovered by digitally filtering the hologram to eliminate all but one sideband, and translating that side band to be centered on zero frequency.

The digital processing performed on a set of 2N+1 measured fields in the pupil (we use 2N+1 measurements rather than N measurements for mathematical convenience, and attempt to expand the spectrum by a factor ≤2N+1) is now discussed. Using a one-dimensional analysis, the kth detected image amplitude can be written as $$A_k(v) = \sum_{n=-N}^{N} p_{k,n} T_o(v - nf_g) rect(v/2f_p). \quad (4)$$

$$k = -N \ldots N$$

where the grating coefficients $p_{k,n}$ change for each of the 2N+1 image captures, the rectangle function represents the finite pupil having a half-width frequency of fp, and we have assumed that the grating frequency is chosen such that $f_g = \sigma f_p$, where σ is an obliquity factor between 0 and 1. In this way, the ±1 diffraction components reside within the pupil, and the grating therefore produces aliasing with overlapping spectral regions. In practice, σ is taken to be between 0.80-0.95. The spectral overlap regions in signal processing is utilized, but this overlap is also needed when extending to 2D with a circular pupil so that complete coverage of the broadened spectral domain is obtained without gaps.

Equation 5 can be rewritten in matrix-vector form as $$\vec{A}(v) = P\vec{T}(v) \quad (5)$$

where $$\vec{A}(v) = \begin{bmatrix} A_{-N}(v) \\ \vdots \\ A_N(v) \end{bmatrix}, \quad (6)$$

$$\vec{T}(v) = \begin{bmatrix} T_o(v + Nf_g) rect(v/2f_p) \\ \vdots \\ T_o(v - Nf_g) rect(v/2f_p) \end{bmatrix}, \quad (7)$$

and P is a (2N+1)×(2N+1) matrix $$P = \begin{bmatrix} p_{-N,-N} & \cdots & p_{-N,N} \\ \vdots & \vdots & \vdots \\ p_{N,-N} & \cdots & p_{N,N} \end{bmatrix}. \quad (8)$$

Now if the grating constants are chosen such that the matrix P is non-singular and well conditioned, then $P^{-1}$ exists and the spectral segments can be separated through $$\vec{T}(v) = P^{-1}\vec{A}(v). \quad (9)$$

Once the individual spectral segments are known, they can be translated to their proper frequency positions in order to synthesize a broader spectrum. Specifically, the image spectrum half-width increases from $f_p$ to $(\sigma N+1)f_p$, where $(\sigma N+1)$ is the resolution gain factor.

During signal post processing, the overlap between adjacent segments can be used to help compute the complex amplitudes for grating orders beyond the first order, which takes into account potential relative phase shifts that can occur during propagation to the image plane. In this way a self-consistent stitching together of the spectral segments is created. More than 2N+1 measurements can be made as a form of oversampling, with the result that the P matrix is no longer square but can still be readily inverted through use of the pseudo-inverse. Lastly, because the imaging system is coherent, no OTF compensation is required, unlike the case of incoherent imaging with structured illumination.

The ideal square P matrix, based on a set of equal-increment grating steps, takes on a simple form with matrix elements given by $\exp[-j2\pi nm/(2N+1)]$ where n is a row index (0 to 2N) and m is a column index (−N to N). This matrix is unitary with an inverse equal to its conjugate transpose. In practice, there are errors in the grating positioning as well as a small phase drift of the interferometer in between exposures. Also, the imaging system may be slightly misaligned so as to impart different average wavefront error to otherwise symmetric diffraction orders. All of these effects conspire to perturb the P matrix from its ideal form.

However, these perturbations can be accommodated by employing a two-pronged approach. First, assume that the center of the signal spectrum is much larger than the wings. In this case, the complex amplitudes of the 0 and ±1 order beams, which pass through the pupil, can be estimated by directly measuring the corresponding spectral peaks. Note that because the imaging system is coherent, the ±1 peaks are not attenuated by the transfer function, making this technique even more attractive compared to the incoherent case. Next, we consider the ±2 order beams. For these diffracted components the coefficients cannot be directly measured in the same way, but they can instead be estimated by finding values that minimize the sum of the squared difference across pixels in regions where the ±1 and ±2 spectral components overlap with one another. This approach can be extended to deal with higher orders.

Following is a description of how to deal with a "non-ideal" transfer function (OTF).

Continuing the notation, we will denote the Fourier coefficients of the grating by $p_n$ and its period by X. The Fourier transform of the object is denoted by $\mathcal{T}(v)$. Therefore, after the signal passes through the grating, we have in the Fourier domain $$\sum_{n=-L}^{L} p_n T(v - n/X), \quad (1)$$

for an appropriate value of L that depends on the bandwidth of $\mathcal{T}(v)$. After passing through the OTF we observe the signal $$Y(v) = \left(\sum_{n=-L}^{L} p_n T(v - n/X)\right) H(v), \quad (2)$$

where H(V) is the OTL.

To recover $\mathcal{T}(v)$, define $Q_n(v)=\mathcal{T}(v-n/X)H(v)$ so that $$Y(v) = \sum_{n=-L}^{L} p_n Q_n(v). \quad (3)$$

The idea is to first recover $Q_n(v)$, and determine $\mathcal{T}(v)$ from knowledge of $Q_n(v)$ and H(v). To this end, a set of linear equations is recorded with respect to the variables $Q_n(v)$ by changing the grating coefficients $p_n$. Denoting by q the vector with nth element $Q_n(v)$ and by P the matrix with the appropriate element $p_n$:

$$y=Pq, \quad (4)$$

where y consists of the observations from the different gratings. To recover q we can invert the matrix P and obtain $$\hat{q}=P^{-1}y. \quad (5)$$

The original spectrum $\mathcal{T}(v)$ can be found. As before, the elements of q are pieced together to form $$\hat{T}(v) = \sum_{n=-L}^{L} \hat{Q}_n(v + n/X). \quad (6)$$

Up until now the same procedure as in the case of an ideal low-pass OTF was followed. Now, substituting the value of $\hat{Q}_n(v)=Q_n(v)$ into (7), the following results:

$$\hat{T}(v) = T(v) \sum_{n=-L}^{L} H(v + n/X). \quad (7)$$

Therefore, if H(v) and X are such that $$\sum_{n=-L}^{L} H(v + n/X) = 1, \quad (8)$$

as a result, $\hat{T}(v)=T(v)$ is found, and no further processing is necessary. With a triangle OTF (8) can be satisfied if X is chosen to be equal to the cutoff of the OTF. When H(v) is an ideal low-pass filter with cutoff X/2, (8) can also be satisfied.

In practice, the OTL may not be an ideal triangle so that (8) may be only appropriately satisfied. In this case, in the noiseless setting $\hat{T}(v)$ of (7) can be divided by $$S(v) = \sum_{n=-L}^{L} H(v + n/X) \quad (9)$$

which will recover T(v) exactly. In the presence of noise, or when S(v) has values that are close to 0, $\hat{T}(v)$ can be multiplied by $$\frac{S(v)}{S^2(v) + \sigma^2}, \quad (10)$$

where $\sigma^2$ is either the noise variance or a small enough constant to move S(v) away from zero.

Note that even if H(v) obtains small values S(v) will generally not become that small if X is chosen appropriately. In practice, X can be chosen so that S(v) is pretty close to 1 and compensate for any deviations by dividing by S(v). Since S(v) is better behaved than H(v) this should be pretty robust to noise.

The following discussion provides details of an experimental embodiment. Although the experimental embodiment provides examples and details regarding various parameters and results, these aspects are not necessarily limiting to the various other embodiments of the present disclosure. An experimental test system with 1-D resolution enhancement, illustrated in FIG. 1 of Appendix F of the underlying U.S. Provisional Patent Application Ser. No. 61/471,205 (to which this document claims benefit and which are fully incorporated herein by reference), has been constructed in order to demonstrate the technique. A He—Ne laser serves as a coherent source, and the beam is split to form a Mach-Zehnder interferometer with the imaging system placed in one arm. A low-cost CMOS camera can be used for off-axis digital holographic detection. For simplicity, a Ronchi ruling is used as the grating in this initial work. Because such a grating has multiple diffraction orders with varying strengths, front-end illumination optics can be implemented to limit the number of transmitted orders and to balance their powers via spatial filtering. The underlying technique, though, will ultimately not rely on such illumination optics. The grating is moved by a piezo-electric actuator in a sequence of equal-increment steps across one period. At each step a digital hologram is captured. The sequence of holograms is post-processed as described in Sections 2 and 3 to yield a much broader image spectrum.

Using a Ronchi grating of 98.4 lp/mm (2500 lp/in) with an illumination system magnification of 1.25 yields an effective grating illumination frequency of 78.7 lp/mm. A variable aperture iris is adjusted to set to the coherent imaging passband cutoff frequency to approximately 100 lp/mm ($NA_0$=0.063). In this way the ±1 orders are able to pass through the imaging system ($\sigma$=0.79), but higher orders are cut off A spatial filter mask in the illumination path restricts the highest orders to ±2 and also approximately equalizes the powers of the diffracted beams.

The object is a standard USAF test target (Group 7, Elements 4-7). Five hologram exposures are recorded while stepping the grating in five equal-increment steps (2.03 µm/step). Digital post processing yields the five separate spectral regions. FIG. 2 of Appendix F of the underlying U.S. Provisional Patent Application Ser. No. 61/471,205 shows the results when the center three regions (0, ±1 orders) are combined, and FIG. 3b of Appendix F of the underlying U.S. Provisional Patent Application Ser. No. 61/471,205 is the corresponding image with horizontally enhanced resolution. The resolution gain factor is 1.8 (i.e., $NA_1$=0.11). The observed new cutoff frequency of 181 lp/mm (Group 7, Element 4) agrees very well with the expected theoretical value of $NA_1/\lambda$=180 lp/mm. Similarly, FIG. 4 of Appendix F of the underlying U.S. Provisional Patent Application Ser. No. 61/471,205 shows the extended spectrum using all five components. In this case the resolution gain factor is 2.6 ($NA_2$=0.16), and the corresponding enhanced image in FIG. 5b of Appendix F of the underlying U.S. Provisional Patent Application Ser. No. 61/471,205 shows the smallest feature set on the test target (228 lp/mm; Group 7, Element 6) to be well within the new cutoff of 259 lp/mm.

Aspects of the instant disclosure are directed toward an approach for extending the resolution of a coherent optical imaging system by applying the principles behind the recently proposed MWC. These aspects can consist of placing a grating near the object and shifting it in a sequence of equal-increment steps. Coherent detection via digital holography allows linear signal processing to be used to de-alias the transmitted spectrum and reconstruct images with a demonstrated resolution gain of 2.6. Higher gains, in the range of 4-5, should be possible by using a Dammann grating with more orders. 2-D enhancement can be obtained by rotating the grating and repeating the measurements.

A typical application, for example, involves the detection of defects in semiconductor mask, or die inspection. The instant invention is also applicable more generally to improving the resolution of microscopes, providing high resolution images with low-cost low-numerical-aperture lenses. Also, the working distance of this system can be greater than that of a conventional microscope with comparable resolution.

This approach allows super-resolution by an arbitrary factor of N, without severe restrictions on the actual imaging system and without the requirement for fluorescent materials. N is likely in the range from 2 to 5. Aspects of the instant disclosure do not need the use of an object stained with fluorescent dye (or intrinsically fluorescent), or the nonlinear dependence of the fluorescence emission rate on the illumination intensity. Aspects of the instant disclosure also do not use illumination through the imaging optics, which introduces a constraint on the system performance. Further, although the signal can be reshaped in phase space, aspects of the instant disclosure allow for the ability to view more bandwidth than that available by the system.

1-D system solutions have been implemented in software based on both coherent and incoherent illumination. The coherent case seems to be versatile in the sense that the grating does not need to physically contact the object being imaged, which is beneficial for implementation, particularly given the fact that the grating must move relative to the object (i.e., to avoid rubbing or scraping of the grating against the object). Other related embodiments and contemplated approaches do not require the grating to be physically moved.

The various embodiments described above and shown in the figures are provided by way of illustration only and should not be construed to limit the disclosure. Based on the above discussion and illustrations, those skilled in the art will readily recognize that various modifications and changes may be made to the present disclosure without strictly following the exemplary embodiments and applications illustrated and described herein. For instance, applications other than grating-enhanced optical imaging may be amenable to implementation using similar approaches. In addition, one or more of the above example embodiments and implementations may be implemented with a variety of approaches, including digital and/or analog circuitry and/or software-based approaches. These approaches are implemented in connection with various example embodiments of the present disclosure. Such modifications and changes do not depart from the true scope of the present disclosure, including that set forth in the following claims.

As discussed above, specific applications and background details relative to the present disclosure are discussed above, in the description below and throughout the references cited herein. The embodiments in the Appendices of the underlying provisional applications may be implemented in connection with one or more of the above-described embodiments and implementations, as well as with those shown in the figures and described below. Reference may be made to these Appendices, which are fully incorporated herein by reference.

What is claimed is:

1. An optical imaging apparatus, comprising:
   a laser-based coherent light source;
   an optical device configured and arranged to pass grated light along an illumination direction from the laser-based coherent light source toward an object plane;
   an illumination modulator for changing angles at which the light, moving toward the object plane, reaches the object plane, wherefrom the light reaches the object plane at different angles;
   a circuit configured and arranged to process image-based data in response to and based on the light reaching the object plane at different angles for a user-viewable image of an object in proximity of the object plane.

2. An optical imaging apparatus, according to claim 1, wherein the optical device includes a grating for passing the light.

3. An optical imaging apparatus, according to claim 1, wherein the optical device includes a uniform grating for passing the light.

4. An optical imaging apparatus, according to claim 1, wherein the optical device includes a segmented grating for passing the light.

5. An optical imaging apparatus, according to claim 1, wherein the optical device is configured and arranged to provide the grated light via segmented grating of the light.

6. An optical imaging apparatus, according to claim 1, wherein the optical device is configured and arranged to provide the grated light via uniform grating of the light.

7. An optical imaging apparatus, according to claim 1, further including a controller configured and arranged to cause the illumination modulator to change the angles.

8. An optical imaging apparatus, according to claim 1, further including a scan mirror system.

9. A method comprising the steps of:
providing a spatially coherent light source for illumination of an object;
generating from a grating component N optical wavefronts containing the object's spatial amplitude variation; and
using an imaging system having an object-space collection numerical aperture of $NA_0$ and using a light-responsive device to detect at least N complex-amplitude images of the composite wavefronts propagating from the object and received by the imaging system.

10. The method of claim 9, further including the step of digital processing of data from the detection of the at least N complex-amplitude images for constructing a resultant high-resolution image.

11. An optical imaging apparatus, comprising:
a spatially coherent light source for illumination of an object;
a grating component configured and arranged to generate N optical wavefronts containing the object's spatial amplitude variation;
an imaging system having an object-space collection numerical aperture of $NA_0$; and
a light-responsive device configured and arranged to detect at least N complex-amplitude images of the composite wavefronts propagating from the object and received by the imaging system.

12. The optical imaging apparatus of claim 11, wherein the grating component is further configured and arranged to cause each of the N optical wavefronts to propagate in one of N different directions.

13. The optical imaging apparatus of claim 12, wherein the angular spectrum associated with each of the N optical wavefronts has a unique bias angle.

14. The optical imaging apparatus of claim 11, wherein the light-responsive device is further configured and arranged for acquiring the complex-amplitude images sequentially in at least N steps and in digital format.

15. The optical imaging apparatus of claim 11, wherein the light-responsive device is further configured and arranged for detecting the complex-amplitude images by digital holography.

16. The optical imaging apparatus of claim 11, further including a digital processing circuit configured and arranged for constructing, from N complex-amplitude images, a resultant high-resolution image.

17. The optical imaging apparatus of claim 16, wherein the resultant high-resolution corresponds to an "effective" numerical aperture $NA_{\text{eff}}$ that is larger than the actual numerical aperture.

18. The optical imaging apparatus of claim 16, wherein the resultant high-resolution corresponds to an "effective" numerical aperture $NA_{\text{eff}}$ that is larger than the actual numerical aperture, such that in the case of 1-D enhancement, $NA_{\text{eff}}$ can be as large as $N*NA_0$.

19. The optical imaging apparatus of claim 16, wherein the resultant high-resolution corresponds to an "effective" numerical aperture $NA_{\text{eff}}$ that is larger than the actual numerical aperture, such that in the case of 2-D enhancement, the resolution gain in a given direction depends on how the N object wavefronts are distributed in angle space.

20. The optical imaging apparatus of claim 16, wherein the resultant high-resolution corresponds to an "effective" numerical aperture $NA_{\text{eff}}$ that is larger than the actual numerical aperture, such that a degree of overlap of the N angular spectra is provided to facilitate post-image-capture stitching of the spectra together in the presence of optical components.

* * * * *